United States Patent [19]
Cooper et al.

[11] Patent Number: 5,479,668
[45] Date of Patent: Jan. 2, 1996

[54] REVOLVING SUNTAN BED

[76] Inventors: Tracey A. Cooper; Richard W. Cooper, Jr., both of 3129 A Liberty, Hill AFB, Utah 84056

[21] Appl. No.: 393,193

[22] Filed: Feb. 23, 1995

[51] Int. Cl.⁶ .............................. A47C 20/00; A61G 7/00
[52] U.S. Cl. .................................... 5/656; 5/600
[58] Field of Search ............... 5/656, 600, 652, 5/657; 297/217.3, 217.7; 607/95

[56] References Cited

U.S. PATENT DOCUMENTS

| | | | |
|---|---|---|---|
| 3,646,896 | 3/1972 | Derjuinsky | 5/656 |
| 4,356,887 | 11/1982 | Fisher et al. | 182/63 |
| 4,379,588 | 4/1983 | Speice | 297/217 |
| 4,441,220 | 4/1984 | Peterson | 5/656 |
| 4,597,119 | 7/1986 | Padgett | 5/656 |
| 4,720,140 | 1/1988 | Change, III | 297/217 |
| 4,824,170 | 4/1989 | Goldmeier | 5/656 |
| 5,078,451 | 1/1992 | Sobel | 5/656 |
| 5,211,172 | 5/1993 | McGuane et al. | 297/217.7 |

Primary Examiner—Alexander Grosz

[57] ABSTRACT

A revolving suntan bed including a generally planar horizontal pedestal; an annular driving gear coupled to the pedestal; a plurality of rotatable rollers coupled to and extended downwards from the pedestal; a rigid base having a central hub axially secured to the pedestal for allowing its revolution, a track axially positioned about the hub for receiving the rollers therein and directing their direction of travel, and a plurality of spokes coupled between the hub and track; and an electric motor having a geared rotatable rotor in mesh with the driving gear and with the motor electrically energizable for imparting rotation to the rotor for revolving the pedestal.

2 Claims, 4 Drawing Sheets

REVOLVING SUNTAN BED

BACKGROUND OF THE INVENTION

1. Field of the Invention

The present invention relates to a revolving suntan bed and more particularly pertains to continuously revolving a user lying thereupon and allowing such user to attain an even tan when the suntan bed is placed under a tanning light source with a revolving suntan bed.

2. Description of the Prior Art

The use of revolving bed mechanisms is known in the prior art. More specifically, revolving bed mechanisms heretofore devised and utilized for the purpose of revolving a user placed thereupon are known to consist basically of familiar, expected and obvious structural configurations, notwithstanding the myriad of designs encompassed by the crowded prior art which have been developed for the fulfillment of countless objectives and requirements.

By way of example, U.S. Pat. No. 3,646,896 to Derujinsky et al. discloses a sunbather's rotatable platform. U.S. Pat. No. 4,356,887 to Fisher et al. discloses a rotatable platform assembly. U.S. Pat. No. 4,379,588 to Speice discloses a revolving solar lounger. U.S. Pat. No. 4,720,140 to Change, III discloses a rotating platform for sunbathers. U.S. Pat. No. 5,211,172 to McGuane et al. discloses a solar-controlled sun tracker for a sunbather.

While these devices fulfill their respective, particular objective and requirements, the aforementioned patents do not describe a revolving suntan bed that allows a user to obtain an even tan and has a pedestal that completes one rotation every twenty minutes.

In this respect, the revolving suntan bed according to the present invention substantially departs from the conventional concepts and designs of the prior art, and in doing so provides an apparatus primarily developed for the purpose of continuously revolving a user lying thereupon and allowing such user to attain an even tan when the suntan bed is placed under a tanning light source.

Therefore, it can be appreciated that there exists a continuing need for new and improved revolving suntan bed which can be used for continuously revolving a user lying thereupon and allowing such user to attain an even tan when the suntan bed is placed under a tanning light source. In this regard, the present invention substantially fulfills this need.

SUMMARY OF THE INVENTION

In the view of the foregoing disadvantages inherent in the known types of revolving bed mechanisms now present in the prior art, the present invention provides an improved revolving suntan bed. As such, the general purpose of the present invention, which will be described subsequently in greater detail, is to provide a new and improved revolving suntan bed and method which has all the advantages of the prior art and none of the disadvantages.

To attain this, the present invention comprises, in combination, a circular horizontal planar rigid pedestal having an upper surface, a lower surface, a periphery interconnecting the surfaces, and a diameter of about 6 feet. A rigid tubular coupling component is included and axially secured to the lower surface of the pedestal and extended downwards therefrom. An annular rigid driving gear is axially aligned with the pedestal and coupled to the lower surface thereof. Six rotatable rollers are included and coupled to and extended downwards from the lower surface of the pedestal in a generally circular configuration between the periphery of the pedestal and the driving gear.

A rigid base is provided. The base has a central cylindrical hub disposed within the coupling component for allowing revolution of the pedestal with respect thereto, an annular rigid horizontal planar bottom wall axially aligned about the hub, a pair of concentrically positioned side walls coupled to and extended upwards from the bottom wall to define an annular track for receiving the rollers therein and directing their direction of travel, and four spokes coupled between the hub and inboard side wall and with each spoke positioned perpendicularly with respect to the adjacently located spokes. An electric motor is provided. The motor is disposed between a pair of spokes and positionable upon a recipient horizontal supporting surface. The motor has a fixed stator and a geared rotatable rotor. The rotor of the motor is in mesh with the driving gear. The motor is electrically energizable for imparting rotation to the rotor. The driving gear and rotor in combination allow the pedestal to complete one revolution every 20 minutes. Lastly, a power cable is included. The power cable has a terminal end coupled to the motor and a plug end extended to a remote location for receiving electrical power from an external electrical source.

There has thus been outlined, rather broadly, the more important features of the invention in order that the detailed description thereof that follows may be better understood, and in order that the present contribution to the art may be better appreciated. There are, of course, additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide a new and improved revolving suntan bed which has all the advantages of the prior art revolving bed mechanisms and none of the disadvantages.

It is another object of the present invention to provide a new and improved revolving suntan bed which may be easily and efficiently manufactured and marketed.

It is a further object of the present invention to provide a new and improved revolving suntan bed which is of durable and reliable construction.

An even further object of the present invention is to provide a new and improved revolving suntan bed which is susceptible of a low cost of manufacture with regard to both materials and labor, and which accordingly is then susceptible of low prices of sale to the consuming public, thereby making such a revolving suntan bed economically available to the buying public.

Still yet another object of the present invention is to provide a new and improved revolving suntan bed which provides in the apparatuses and methods of the prior art some of the advantages thereof, while simultaneously overcoming some of the disadvantages normally associated therewith.

Even still another object of the present invention is to provide a new and improved revolving suntan bed for continuously revolving a user lying thereupon and allowing such user to attain an even tan when the suntan bed is placed under a tanning light source.

Lastly, it is an object of the present invention to provide a new and improved revolving suntan bed comprising a generally planar horizontal pedestal; an annular driving gear coupled to the pedestal; a plurality of rotatable rollers coupled to and extended downwards from the pedestal; a rigid base having a central hub axially secured to the pedestal for allowing its revolution, a track axially positioned about the hub for receiving the rollers therein and directing their direction of travel, and a plurality of spokes coupled between the hub and track; and an electric motor having a geared rotatable rotor in mesh with the driving gear and with the motor electrically energizable for imparting rotation to the rotor for revolving the pedestal.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein.

The same reference numerals refer to the same parts through the various Figures.

DESCRIPTION OF THE PREFERRED EMBODIMENT

Figure 1:
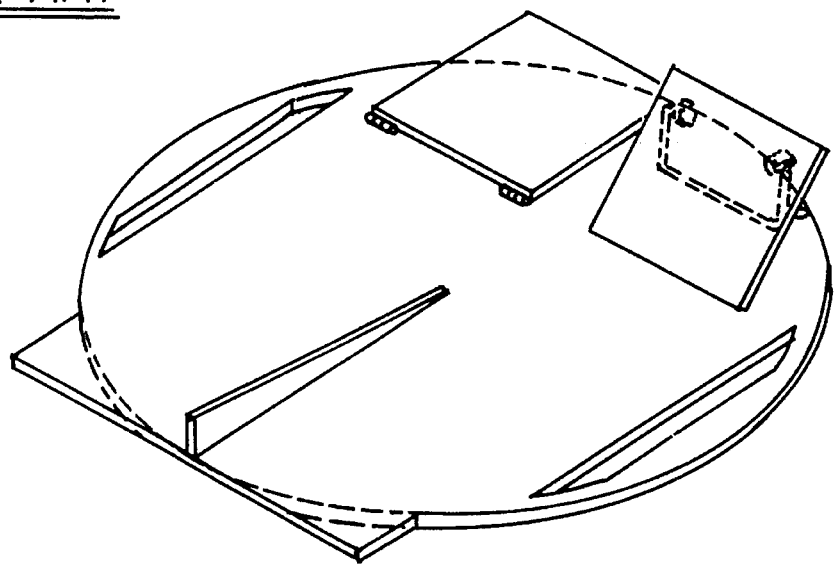
FIG. 1 is a perspective view of a prior art sunbather's rotatable platform.
Figure 2:
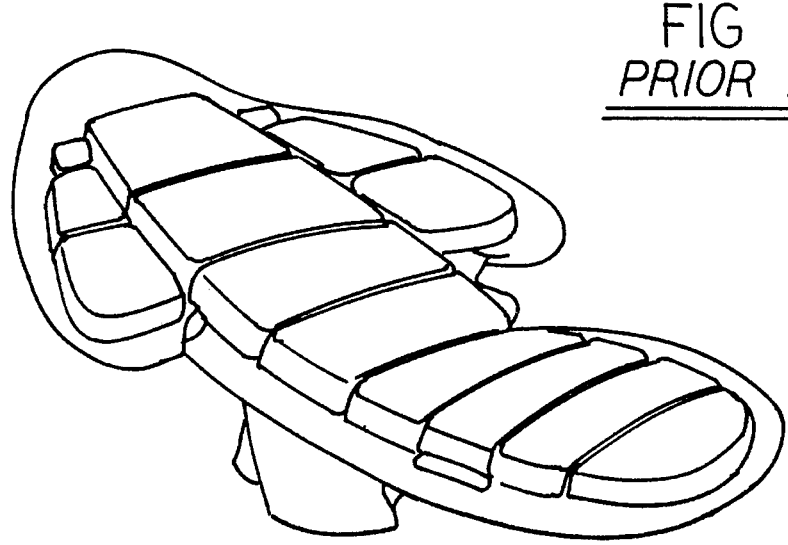
FIG. 2 is a perspective view of a prior art revolving solar lounger.

With reference now to the drawings, and in particular, to FIG. 1 thereof, the preferred embodiment of the new and improved revolving suntan bed embodying the principles and concepts of the present invention and generally designated by the reference number 10 will be described.

The present invention is comprised of a plurality of components. In their broadest context, such components include a pedestal, a driving gear, a set of rollers, a base, and a motor. Such components are individually configured and correlated with respect to each other to provide the intended function of continuously revolving a user 11 lying thereupon and allowing such user to attain an even tan when the suntan bed is placed under a tanning light source.

Specifically, the present invention includes a pedestal 12. The pedestal is circular and planar in structure and positioned in a horizontal plane. The pedestal is formed of a rigid material such as fiberglass or plywood. The pedestal has an upper surface 14, a lower surface 16, and a periphery 18 interconnecting the surfaces. The pedestal has a diameter of about 6 feet. A mattress or similar cushioning type mechanism can be disposed upon the pedestal for providing a user additional comfort.

Figure 6:
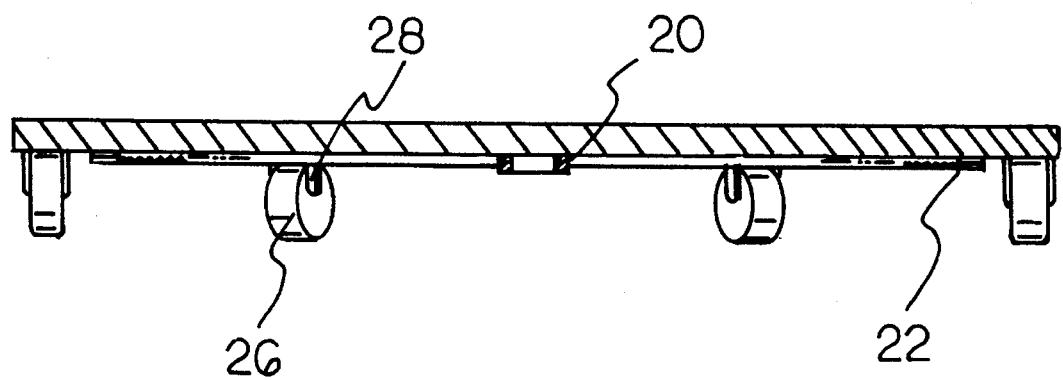
FIG. 6 is a cross-sectional view of the present invention taken along the line 6—6 of FIG. 3.

A tubular coupling component 20 is included as shown in FIG. 6. The tubular coupling component is formed of a rigid material such as metal. The coupling component is axially secured to the lower surface of the pedestal and extended downwards therefrom. The tubular coupling component thus defines the central point of rotation for the pedestal.

Figure 7:
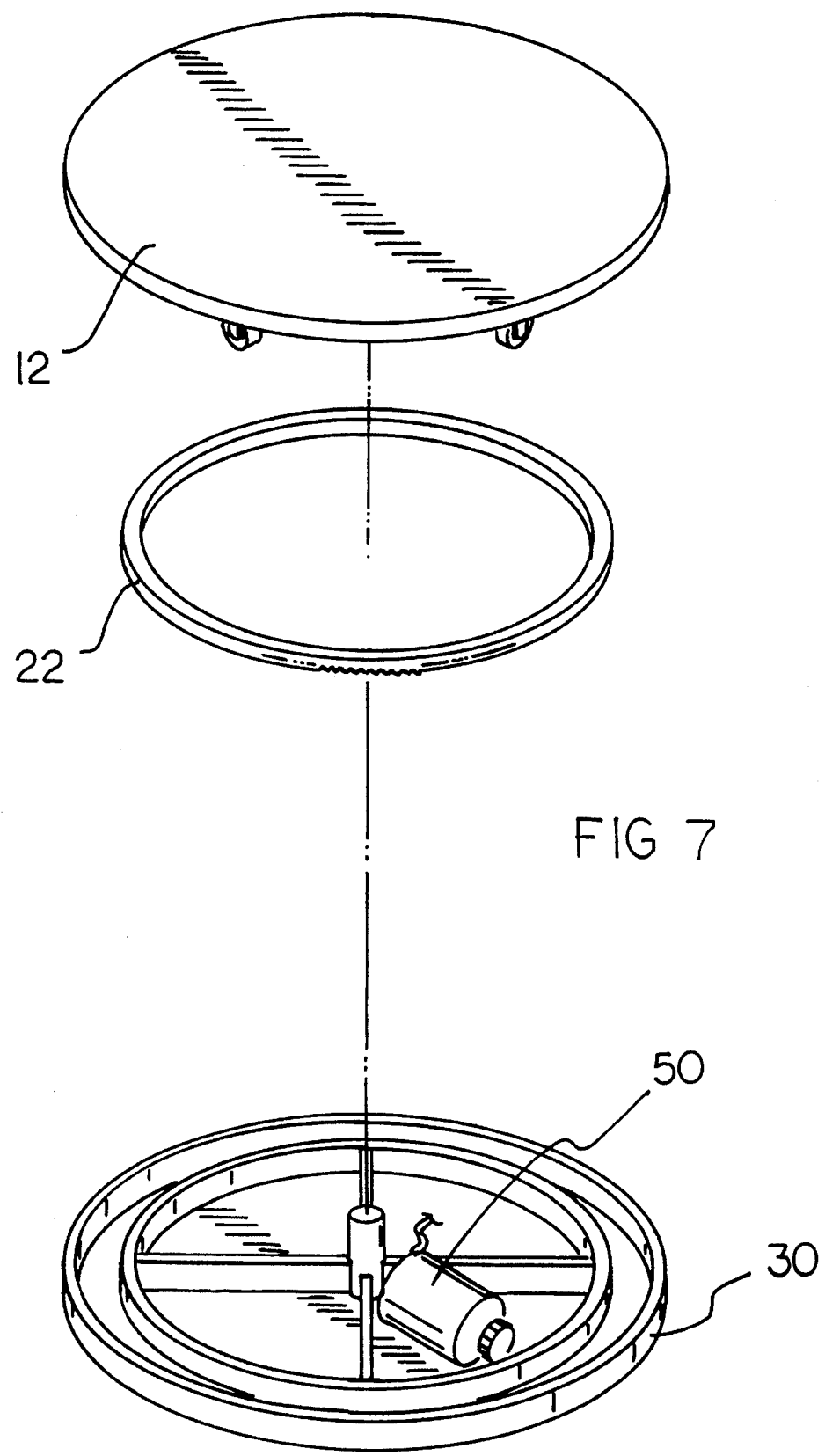
FIG. 7 is an exploded perspective view of the present invention.

Also included is a driving gear 22 as shown in FIG. 7. The driving gear is of an annular structure and has a plurality of teeth formed therearound. The driving gear is formed of metal or other similar rigid material. The driving gear is axially aligned with the pedestal and coupled to the lower surface thereof.

Six rollers 24 are extended downwards from the lower surface of the pedestal. Each roller consists of a rotatable wheel 26 held in place by a generally U-shaped support bracket 28. The rollers are positioned in a generally circular configuration at a location between the periphery of the pedestal and the outer radial extent of the driving gear. The support bracket of each roller is coupled to the lower surface of the pedestal such that it can swivel. The rollers allow the pedestal to be moved with ease. The rollers also retain the pedestal in a generally horizontal orientation for use.

Figure 3:
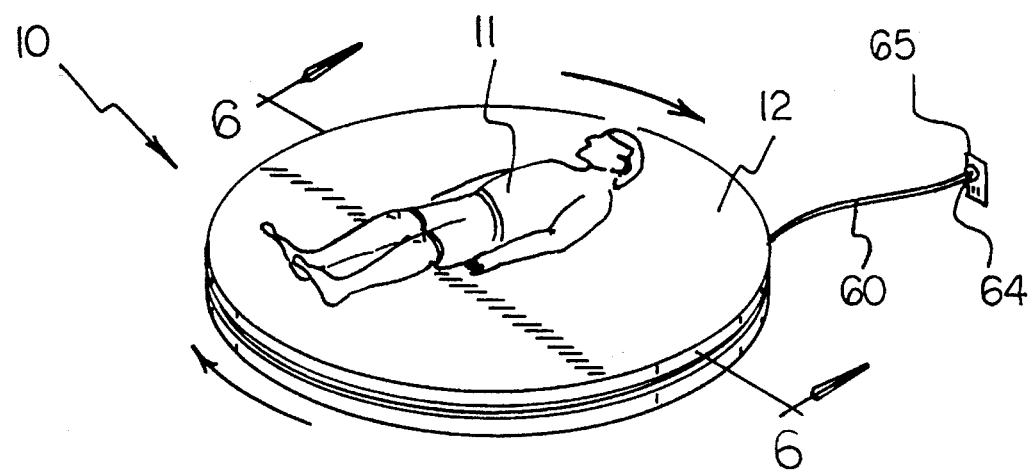
FIG. 3 is a perspective view of the preferred embodiment constructed in accordance with the principles of the present invention with a user lying thereupon.
Figure 4:
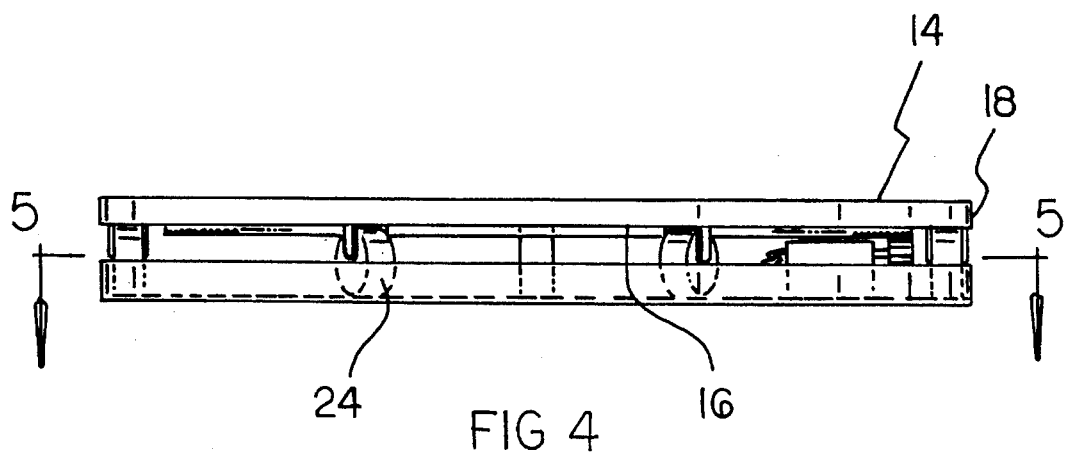
FIG. 4 is a side-elevational view of the present invention.
Figure 5:
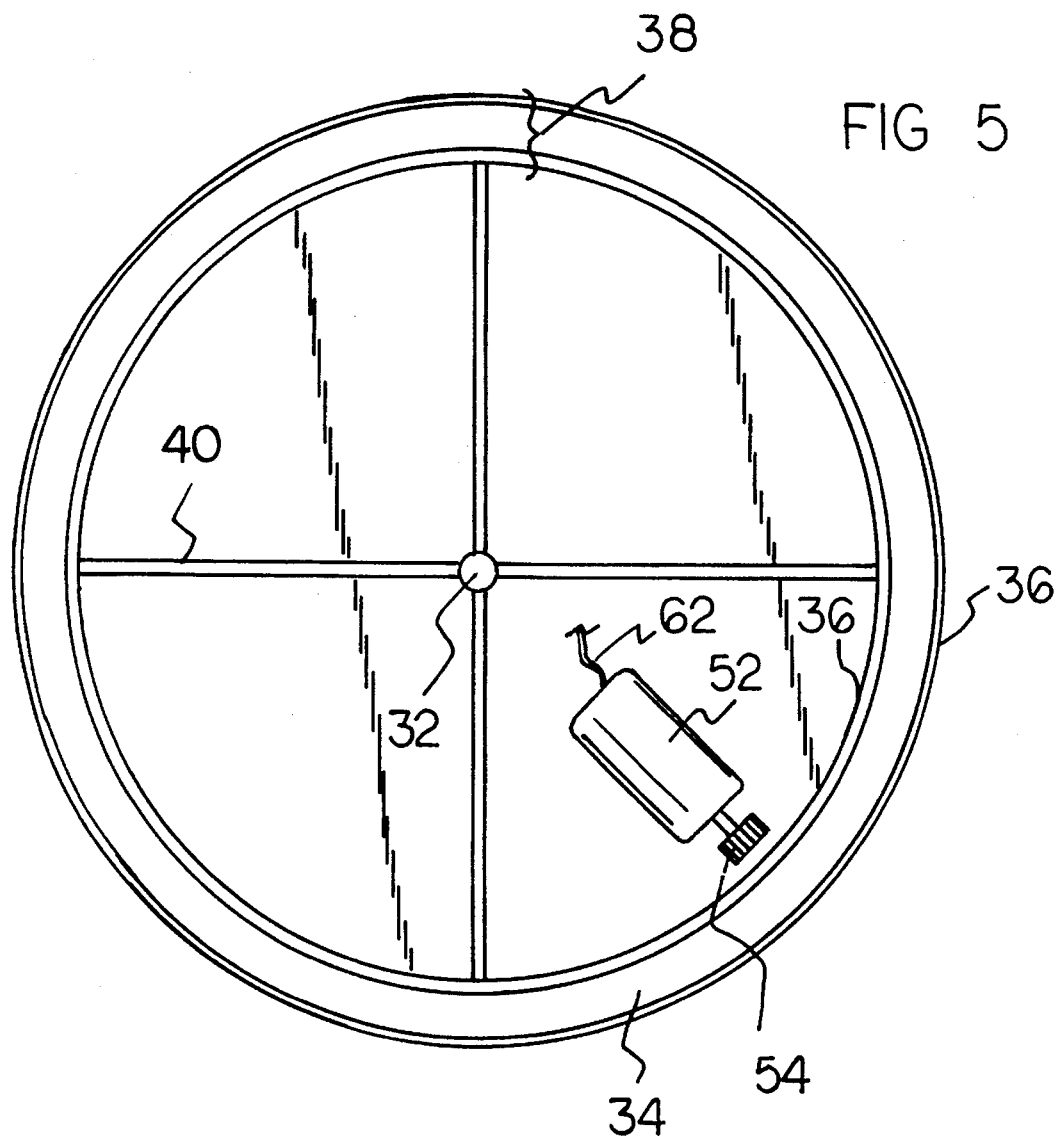
FIG. 5 is a plan view of the present invention with its pedestal removed.

To further support the pedestal, a base 30 is included. The base is formed of a rigid material such as fiberglass or wood. The base has a central cylindrical hub 32 axially aligned with and disposed within the coupling component 20. The hub allows revolution of the pedestal and also supports the central extent thereof. The base also includes an annular horizontal planar bottom wall 34. The bottom wall is axially aligned about the hub. In addition, the base includes a pair of concentrically positioned side walls 36. The side walls are coupled to and extended upwards from the inner and outer extents of the bottom wall to define an annular track 38 as shown in FIG. 5. The inboard wall has an outer radial extent less than the inner radial extent of the driving gear. The outboard wall has an inner radial extent greater than the outer radial extent of the driving gear. The track formed by the side walls and bottom wall is used for receiving the rollers therein and directing their direction of travel upon the bottom wall 34 in a circumferential fashion. The outboard side wall has an outer radial extent essentially equal to the radial extent of the pedestal. Thus, as shown in FIG. 3, the outer surface of the outboard side wall is placed in a position flush with the periphery of the pedestal. To provide rigidity to the base, four linear spokes 40 are coupled between the hub and inboard side wall. Each spoke is positioned perpendicularly with respect to the adjacently located spokes.

An electric motor 50 is disposed between a pair of the spokes as shown in FIG. 5. The electric motor is positionable upon a recipient horizontal supporting surface such as a floor. The motor has a fixed stator 52 and a geared rotatable rotor 54. The rotor is in mesh with the teeth on the driving gear 22. The motor is electrically energizable for imparting rotation to the rotor. The driving gear and rotor in combination define a gear configuration with a ratio that allows the pedestal to complete one revolution every 20 minutes. Lastly, a sheathed power cable 60 is provided. The power cable has a terminal end 62 and a plug end 64. The terminal end 62 is coupled to the stator of the motor. The plug end 64 is extended to a remote location for receiving electrical power from an external source such as a conventional household wall socket 65.

The present invention is a tanning bed that helps to minimize any shadowing on a user by continuously revolving the user lying on it at a very slow speed. The present invention consists of a pedestal, a base, a driving gear, a set of rollers, and an electric motor. The bed is fabricated from either heat resistant fiberglass or plywood and is roughly 6 feet in diameter. The base has similar dimensions, but is made from aluminum or another suitable metal alloy. Enabling the bed to rotate freely on its axis is the central hub, which is only a few inches high. The underside of the pedestal has a toothed gear coupled thereto for engagement with the geared rotor of the motor. Beneath the pedestal is smooth track to accommodate the rollers. The motor has a matching gear on it that drives the bed in one direction. Gearing is designed so that the bed completes one revolution every 20 minutes. There are six rollers equally spaced on their support braces. They enable the smooth revolution of the pedestal.

To use the present invention for obtaining an even tan, the unit is simply moved under a tanning light source such as the sun or ultraviolet light and plugged into any standard electrical outlet. An even tan is almost guaranteed because the rotation virtually eliminates shadowing. The present invention offers people who enjoy sun tanning a method for achieving an even tan. It is comfortable, portable, and large enough to be used by most anyone. The present invention thus precludes a user from having to continually move a blanket or towel to adjust to the position of a light source for tanning.

As to the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and the manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modification and changes will readily occur to those skilled in the art, it is not desired to limit the invention to the exact construction and operation shown and described, and accordingly, all suitable modification and equivalents may be resorted to, falling within the scope of the invention.

What is claimed as being new and desired to be protected by Letters Patent of the United States is as follows:

1. A revolving suntan bed for continuously revolving a user lying thereupon and allowing such user to attain an even tan when the suntan bed is placed under a tanning light source comprising, in combination:

a circular horizontal planar rigid pedestal having an upper surface, a lower surface, and a periphery interconnecting the surfaces, and a diameter of about 6 feet;

a rigid tubular coupling component axially secured to the lower surface of the pedestal and extended downwards therefrom;

an annular rigid driving gear axially aligned with the pedestal and coupled to the lower surface thereof;

six rotatable rollers coupled to and extended downwards from the lower surface of the pedestal in a generally circular configuration between the periphery of the pedestal and the driving gear;

a rigid base coextensive with the pedestal and having a central cylindrical hub disposed within the coupling component for allowing revolution of the pedestal with respect thereto, an annular rigid horizontal planar bottom wall axially aligned about the hub, inboard and outboard concentrically positioned side walls coupled to and extending upwards from the bottom wall to define an annular track for receiving the rollers therein and directing their direction of travel, and four spokes coupled between the hub and inboard side wall and with each spoke positioned perpendicularly with respect to the adjacently located spokes; and an electric motor disposed between a pair of spokes and positionable upon a recipient horizontal supporting surface, the motor having a fixed stator and a geared rotatable rotor in mesh with the driving gear and with the motor electrically energizable for imparting rotation to the rotor, the driving gear and rotor in combination designed to allow the pedestal to complete one revolution every 20 minutes.

2. The revolving suntan bed as set forth in claim 1, further comprising a power cable having a terminal end coupled to the motor and a plug end extended to a remote location for receiving electrical power from an external source.

\* \* \* \* \*